United States Patent [19]

Brodman et al.

[11] Patent Number: 5,414,198

[45] Date of Patent: May 9, 1995

[54] **DEGRADATION OF NITROCELLULOSE BY COMBINED CULTURES OF *SCLEROTIUM ROLFSII* ATCC 24459 AND FUSARIUM SOLANI IFO 31093**

[75] Inventors: Bruce W. Brodman, Stroudsburg; Anil Sharma, Yardley, both of Pa.; Thiruvenkataswamy Shanmugasundaram, Flanders; Ying-Zhi Zhang, Wharton, both of N.J.

[73] Assignee: The United States of America as represented by the Secretary of the Army, Washington, D.C.

[21] Appl. No.: 289,813

[22] Filed: Aug. 12, 1994

[51] Int. Cl.$^6$ ............................ C12N 1/00; C12N 1/14
[52] U.S. Cl. ................................. 588/202; 149/124; 588/203; 435/262.5; 435/911; 435/929
[58] Field of Search ................. 149/124; 588/202, 203; 435/262.5, 929, 911

[56] References Cited

U.S. PATENT DOCUMENTS

| | | | |
|---|---|---|---|
| 3,616,222 | 10/1971 | Dasinger et al. | 195/33 |
| 3,972,775 | 8/1976 | Wilke et al. | 195/33 |
| 5,006,126 | 4/1991 | Olson et al. | 8/401 |

*Primary Examiner*—Donald P. Walsh
*Assistant Examiner*—Anthony R. Chi
*Attorney, Agent, or Firm*—Anthony T. Lane; Edward Goldberg; John E. Callaghan

[57] ABSTRACT

The invention provides a method of degrading nitrate esters by exposing a suspension of a nitrate ester to a combined culture of *Sclerotium rolfsii* ATCC 24459 and *Fusarium Solani* IFO 31093. This allows an alleviation of environmental difficulties associated with the demilitarization of nitrocellulose base gun propellants and for the bioremediation of soils contaminated with such nitrocellulose based materials.

21 Claims, No Drawings

DEGRADATION OF NITROCELLULOSE BY COMBINED CULTURES OF *SCLEROTIUM ROLFSII* ATCC 24459 AND FUSARIUM SOLANI IFO 31093

GOVERNMENTAL INTEREST

The invention described herein may be manufactured, used and licensed by or for the Government for Governmental purposes without the payment to us of any royalties thereon.

BACKGROUND OF THE INVENTION

1. Field of the Invention

The present invention relates to a process for alleviating environmental difficulties associated with the demilitarization of nitrocellulose base gun propellants. More particularly it provides a method for the bioremediation of soils contaminated with such materials.

2. Description of the Prior Art

The nitrate ester of cellulose, also known as nitrocellulose and cellulose nitrate, is the most commonly used energetic ingredient in gun propellant compositions. Nitrocellulose has a limited shelf life because of an auto catalytic decomposition reaction which can occur over long periods of time while in ambient storage. This reaction becomes dangerous when the stabilizer (diphenylamine), present in the propellant composition, is depleted. Each year large quantities of scrap propellant must be disposed of, but it has long been a problem to safely dispose of nitrocellulose based gun propellants. The currently employed disposal method involves an open air burning of these materials. Unfortunately, both the air borne particulates and the pan residues resulting from open air burning are toxic. When these materials are incinerated the resulting toxic pan residues must be treated as a hazardous waste. Even such treated materials produce toxic particulates and probably will not meet future EPA requirements. Current remediation techniques use mobile incinerators to destroy the energetic materials present in contaminated soils. The soil must be dug up to a depth of six feet and the material incinerated. Obviously, this method is very costly and time consuming. For this reason it is desired to develop a microbial method that could result in the mineralization of this material. Early investigations of the biodegradation of nitrocellulose came to the conclusion that nitrocellulose was not directly attacked by microorganisms, but rather degraded by acidic metabolites resulting from their growth.

A number of chemical processes utilizing inorganic sulfides and hydrides have been investigated for the degradation of nitrocellulose. U.S. Pat. No. 4,814,439 teaches a method for nitrocellulose degradation which uses organic sulfhydryl compounds to release the nitrogen from nitrocellulose in the form of inorganic nitrite ions. Nitrocellulose has been shown to be decomposed by acid treatment and yet more readily by alkaline treatment Wendt, T. M. and A. M. Kaplan, "Chemical-Biological treatment process for cellulose nitrate disposal"; J. Water Poll Control Fed. 48:660–668 (1976) reported that a solution resulting from alkaline hydrolysis could efficiently be treated by a combination of anaerobic and aerobic activated sludge process. Hsieh, H. N. and F. J. Tai, "Anaerobic digestion and acid hydrolysis of nitrocellulose", Proceedings on nitrocellulose— fines, separation and treatment, U.S. Army—Purdue University, West Lafayette, Ind. pp. 110–121 (1993), have shown that 99% of nitrocellulose could be converted into sugars by a single stage acid hydrolysis at 70° C. for 45–60 minutes. Earlier work carried out on microbial degradation of nitrocellulose has produced conflicting results. Bokorny, T., Chemistry and Technology, Pergamon Press, London, England, p. 313 (1965), showed that molds could grow on nitrocellulose suspended in aqueous medium containing mineral salts. Malenkovic, B. and Jacque, M. Chemistry and Technology, Pergamon Press, London, England, p. 313 (1965) suggested that molds were capable of utilizing the dissolved mineral salts but incapable of attacking nitrocellulose. Brodman, B. W. and M. P. Devine, "Microbial attack of nitrocellulose", J. Appl. Polymer Sci. 26: 997–1000 (1981) showed that *Aspergillus fumigatus* could utilize nitrocellulose containing 11.11% nitrogen. They also indicated that the organism did not utilize the nitrogen directly from nitrocellulose but rather relied on a hydrolysis reaction for a source of nitrogen. Investigations carried out by Kaplan, D. L., et al, "Denitrification of high nitrate loads—Efficiencies of alternate carbon sources" International Biodeterioration 23: 233–248 (1987), have shown that nitrocellulose was not subjected to direct microbial attack and their studies indicated that chemical pre-treatment of nitrocellulose was necessary to generate a modified denitrated polymer that could be attacked by microorganisms. IL'Inskaya, A. N. et al "Growth of microorganisms on cellulose nitro-esters", Biotekhnologiya, 4:495–500 (1988) showed that *Aspergillus fumigatus* F-316 was capable of forming reducing sugars from nitrocellulose with a nitrogen content of 11.9% and the fungus utilized the nitrate esters group when subjected to nitrogen deficiency. The same authors further reported the possibility of de-esterification of cellulose nitrate esters by using immobilized *A. fumigatus* and *Pseudomonas fluorescens*. IL'Inskaya, O. N. et al, "Decomposition of nitrocellulose by a community of microorganisms immobilized on it", Biol Nauki. 6:87–91 (1988), did not observe any nitrocellulose degradation when six immobilized *Pseudomonas* sps. and anaerobic cellulolytic bacteria were tested. Duran, M., et al. "Anaerobic biotransformation of nitrocellulose", Proceedings on nitrocellulose—fines, separation and treatment, U.S. Army—Purdue University, West Lafayette, Ind. pp. 92–108 (1993), reported nitrocellulose degradation under anaerobic conditions in a two stage feed reactor. Studies carried out by Hsieh, H. N. and F. J. Tai, "Anaerobic digestion and acid hydrolysis of nitrocellulose" in Proceedings on nitrocellulose—fines, separation and treatment, U.S. Army—Purdue University, West Lafayette, Ind. pp. 110–121 (1993), indicated that only small amount of nitrocellulose could be degraded in a conventional anaerobic digestor.

Under aerobic conditions the present invention has accomplished a 35% nitrocellulose degradation in unoptimized cultural conditions. Significant activities of cellulolytic and denitrifying (nitrate and nitrite reductase) enzymes were detected in growing cultures. The present invention, therefore, provides a more environmentally friendly and less costly route to the demilitarization of nitrate esters and the remediation of soils contaminated by these materials and provides a microbial approach to nitrocellulose degradation. It has now been found that nitrate esters can be biodegraded by a process which uses two specific fungi. This biodegradation can be done either with and without the presence of a surfactant. A surfactant provides an advantage in solubilizing the enzymes produced by the microorganisms.

The degradation process results in the conversion of the nitrocellulose to innocuous products. This method provides an efficient, cost effective and safe technique for the destruction of nitrate esters. The invention uses enzymes which are known to be very specific and efficient catalysts and capable of reactions that can not be achieved by conventional chemical or physical methods. Further, these reactions are accomplished at room temperature which makes them ideally suited for use with labile energetic materials. The invention uses enzymes produced by two microorganisms *Fusarium solani* IFO 31093 and *Sclerotium rolfsii* ATCC 24459 to accomplish the degradation of nitrate esters. While it has been a commonly held belief that nitrocellulose cannot be degraded under aerobic conditions, new and unexpected results are obtained by this invention whereby nitrocellulose can be aerobically degraded.

SUMMARY OF THE INVENTION

The invention provides a method for degrading nitrate esters which comprises forming a suspension of a nitrate ester. Then providing a combination of at least one cellulolytic fungus and at least one denitrifying fungus on a culture growing medium. One contacts the combination with the suspension of nitrate ester and maintains the contact for a sufficient time and under conditions sufficient to support lysis and denitrification of the nitrate ester.

DETAILED DESCRIPTION OF THE PREFERRED EMBODIMENT

The invention provides a method for degrading nitrate esters such as nitrocellulose and nitroglycerine by the use of enzymes produced by a cellulolytic fungus such as *Sclerotium rolfsii* ATCC 24459, and a denitrifying fungus such as *Fusarium solani* IFO 31093. This is performed under aerobic microbial conditions. *Sclerotium rolfsii* ATCC 24459 may be obtained from The American Type Culture Collection, 12301 Park Lawn Drive, Rockville, Md. 20852. *Fusarium solani* IFO 31093 may be obtained from the Institute for Fermentation, 17-85 Juso-Honmachi, 2-Chome Yodagawa-Kw, Osaka, 532, Japan. *Sclerotium rolfsii* ATCC 24459 and *Fusarium solani* IFO 31093 were tested alone and in combination for nitrocellulose degrading activity in liquid medium. It was found that a combination of *S. rolfsii* ATCC 24459 and *F. solani* IFO 31093 significantly degraded nitrocellulose in a given incubation period in submerged cultivation. The combination of cellulolytic and denitrifying fungi was able to grow and significantly degrade nitrocellulose.

In the process, both microorganisms are homogenized and placed in an aqueous medium which contain all required nutrients with the exception of nitrogen. The *Fusarium solani* IFO 31093 and *Sclerotium rolfsii* ATCC 24459 use the nitrocellulose as a nitrogen source. A suspension, preferably an aqueous suspension of the nitrocellulose is formed which in a preferred embodiment also includes a surfactant to facilitate the transport of the enzymes to suspended nitrocellulose. The nitrocellulose nitrogen content can vary over a wide range extending from slightly above 0% up to a maximum nitrogen content of about 14.15%. Typically, the nitrogen content of the nitrocellulose used in gun propellant compositions ranges from about 9% to about 13.3% and most preferably from about 13.1% to about 13.2%. The surfactant is preferably a non-ionic surfactant. The nitrocellulose suspension contacts the fungi containing medium for a sufficient time and under conditions suitable to enable nitrocellulose degradation. Suitable conditions include exposure to air at room temperature. A typical total reaction time is approximately three days or more, preferably from about three to about ten days and most preferably from about three to about seven days. The reaction can be carried out either in a batch or continuous process. It is preferred to maintain a pH range of from about 6 to about 8 during the reaction, however, this is not critical. It is preferred to maintain a temperature in the range of from about 70° F. to about 75° F. during the reaction, however, this is also not critical. Degradation products of the reaction include gaseous ammonia, $CO_2$ and water.

The following non-limiting examples serve to illustrate the invention.

EXAMPLE 1

*Sclerotium rolfsii* ATCC 24459, available from the American Type Culture Collection, Rockville, Md. and *Fusarium solani* IFO 31093, available from the Institute for Fermentation, Osaka, Japan are maintained at 4° C. on Sabourand maltose agar plates with monthly transfers. Nitrocellulose is evaluated for moisture content and then sterilized. Nitrocellulose (smokeless grade) containing 13.17% nitrogen and 25.07% moisture is available from Hercules, Inc., Kenvil, N.J. The desired nitrogen content of the nitrocellulose is typically achieved by blending two different grades of commercially obtainable nitrocellulose. Nitrocellulose may be produced by nitrating cotton linters, wood or other forms of cellulose. Nitrating may be done by mixing the cellulose with a blend of sulfuric and nitric acids in an exothermic reaction requiring cooling for reaction control. Such reaction procedures are well known in the art.

The moisture content of nitrocellulose can be estimated using Du Pont Thermal Analysis System 1090 B equipped with a Thermogravimetric Analyzer 951. It was found that steam sterilization (15 psi, 121° C., 30 minutes) of nitrocellulose released a significant quantity of free nitrite ions indicating decomposition of nitrocellulose. Therefore, ultraviolet (254 nm) treatment was listed as an alternative for nitrocellulose sterilization. UV irradiation of nitrocellulose for 45 minutes does not release free nitrite ions. Hence, nitrocellulose was sterilized for 45 minutes using UV light and then added to the cooled steam sterilized medium.

Inoculum preparation:

Mycelial mats were pregrown in mineral salts medium containing $NaNO_3$ (1.0%) as a nitrogen source and xylan (0.1%) as a carbon source. The mineral salts growth medium contained (g/L): $KH_2PO_4$, 1.0; $MgSO_4$, 0.5; NaCl, 0.1; $CaCl_2$, 0.1 and trace metal solution, 100 microliter. Trace metal salts solution contained (w/v%): $C_6H_8O_7$ (citric acid), 5.0; $ZnSO_4$, 5.0; $CuSO_4$, 0.25; $MnSO_4$, 0.25; $H_3PO_4$, 0.05; $Na_2MoO_4 \cdot 2H_2O$, 0.05 and $CoCl_2$, 2.0. Fungi were grown at 28° C. in a gyrotary shaker (~150 rpm) for 4 days and harvested by centrifugation (5000 rpm, 4° C., 10 min). The harvested fungal mycelia were washed under aseptic conditions with cooled basal salts medium lacking carbon and nitrogen sources. The washed fungal mycelia were then homogenized using Virtishear explosion proof pilot homogenizer operated at half of the maximum output for 2 min at 4° C. with 15 second interruptions.

Biomass dry weight determination:

A known volume of homogenized mycelia used for inoculation was separately filtered through a preweighed filter paper (5.5 cm), washed with distilled water and dried at 105° C. until a constant weight was reached.

Cultural Conditions:

A known volume of homogenized mycelia (~10 mg dry wt) was transferred to the experimental medium (50 ml in 250 ml Erlenmeyer flasks) containing nitrocellulose (0.3%) as a nitrogen source and starch (0.1%) as a co-substrate and incubated in the presence or absence of Makon NF-5 (50 ppm), a non-ionic surfactant, for various time intervals (0, 3, 7, 14, 28 days) in a gyrotary shaker (~150 rpm, 28° C.). Equal volumes of each homogenized fungal culture (1:1) were used whenever a combination of culture was used as a source of inoculum. Two types of control were run in parallel to the treatment, one of them containing $NaN_3$ (1 mM), $HgCl_2$ (1 mM) along with cultures while the other lacked cultures and fungicidal agents. The fungal biomass was harvested at desired time intervals by centrifugation (8000 rpm, 15 min, 4° C.). The biomass and the supernatant were subjected to further analyses.

Preparation of crude fungal enzyme:

The fungal mycelia which were cultivated and harvested as described above were washed with excess of potassium phosphate buffer (100 mM, pH 7.0) and then resuspended in 5 ml of potassium phosphate buffer (100 mM, pH 7.0) containing phenylmethylsulfonyl fluoride (approx. 2 microliter, 0.1 mM) and ground in a homogenizer, operated at half of the maximum speed for 3 min with 30 second interruptions. The homogenate was then centrifuged (10,000 rpm, 20 min., 4° C.) and the supernatant analyzed for intra-cellular (nitrate and nitrite reductases) enzymes.

Cellulases:

i) Carboxy-methyl cellulase (EC 3.2.1.4) was assayed as described by Mandels, M. and J. Weber, in "Cellulases and their applications", Gould, R. F., ed. Adv. Chem. Ser., American Chemical Society, Washington, D.C. 95:391–414 (1969). Reducing groups generated were estimated by Somogyi reagent. One unit of carboxy-methyl cellulase was defined as the amount of enzyme which generates 1 micromole of glucose equivalent per minute. ii) Filter paper cellulase (EC 3.2.1.9) was assayed similarly. Reducing groups generated were estimated by Somogyi reagent. One unit of filter paper cellulase was defined as the amount of enzyme which generates 1 micromole of glucose equivalent per minute.

Alpha-Amylase:

(EC 3.2.1.1) was assayed as described by Bernfeld, D., in "Amylases alpha and beta" Methods in Enzymology, Colowick, S. P. and N. O. Kaplan, eds. Academic Press, NY. 1: 149–158 (1955). Reducing groups generated were estimated by using Somogyi reagent. One unit of amylolytic activity was defined as the amount of enzyme which generates 1 micromole of glucose equivalent per minute.

Beta-Glucosidase (EC 3.2.1.21) was assayed as described by Kubackova, M. S., et al, in "Purification of xylanase from the wood rotting fungus, Trametes hirsuta". Folia Microbiol. 21: 28–35, using p-nitrophenyl beta-D glucopyranoside. One unit of beta-glucosidase was defined as the amount of enzyme releasing under given conditions 1 micromole of p-nitrophenol from the substrate.

Nitrate reductase (EC 1.6.6.2) was assayed by measuring the reduction of nitrate to nitrite colorimetrically described by MacGregor, C. H., "Isolation and characterization of nitrate reductase from *E. coli*"; Methods in Enzymology. Colowick, S. P. and N. O. Kaplan, eds. Academic Press, NY. L III: 347–355 (1978), using potassium nitrate as a substrate and methyl viologen as an artificial electron donor. One unit of nitrate reductase was defined as the amount of enzyme producing 1 micromole of nitrite per min at 25° C.

Nitrite reductase (EC 1.6.6.4) was assayed by the procedure of Kakutani, T. et al, "Purification and properties of a copper containing nitrite reductase from a denitrifying bacterium *Alcaligenes faecalis* strain S-6", J. Biochem. 89:453–461 (1981), using potassium nitrite as a substrate and methyl viologen as a hydrogen donor. One enzyme unit was defined as the amount of enzyme required to reduce 1 micromole of nitrite per minute at 25° C.

Determination of biomass and unutilized nitrocellulose:

Medium containing nitrocellulose and grown fungi was filtered through a preweighed filter paper (VWR Scientific), 5.5 cm, (W1) and the filter cake was washed thoroughly with distilled water, dried at 50° C. for 3 hours and cooled at room temperature (22° C.) in a desiccator having Drierite. The filter paper with filter cake was dried and weighed until constant weight was attained (W2). The dried filter cake was then transferred to a preweighed centrifuge tube (W3). Both the tube with the filter cake (W4) and the filter paper from which the filter cake was removed (W5) were weighed. Acetone was added gradually with vigorous stirring until almost all nitrocellulose in the filter cake dissolved. The acetone nitrocellulose solution with suspended biomass was centrifuged (8000 rpm, 15° C., 1 hour) and the supernatant transferred to another preweighed centrifuge tube (W6). Water was added to the supernatant to precipitate dissolved nitrocellulose and the suspension was recentrifuged for 1.5 hour. Supernatant was then transferred to a flask. Acetone was added to the residue containing the biomass with vigorous mixing and was subsequently centrifuged as described above. The supernatant was then transferred to the centrifuge tube containing nitrocellulose. The biomass residue in the centrifuge tube was dried at 50° C. for 3 hours and cooled in a desiccator having Drierite. The procedure was repeated until constant dry weight was attained (W7). Water was added to the supernatant obtained from biomass centrifugation to precipitate nitrocellulose. The suspension was centrifuged for 1.5 hours and the supernatant transferred to a flask. Residual nitrocellulose in the centrifuge tube was dried at 50° C. for 3 hours and cooled in a desiccator having Drierite. Nitrocellulose samples were dried and weighed until a constant weight (W8) was attained. The residual nitrocellulose and biomass were determined as follows:

$$\text{Weight of Biomass} = \frac{(W2 - W1)(W7 - W3)}{W4 - W3}$$

$$\text{Weight of Nitrocellulose} = \frac{(W2 - W1)(W8 - W6)}{W4 - W3}$$

Correction factors for biomass and nitrocellulose determinations:

In order to establish a correction factor for biomass determination, certain amounts of biomass (20, 50, 100, 200, and 300 mg) were extracted with acetone and centrifuged as described earlier. The supernatant was discarded and the residual biomass was dried and weighed. Based on the results, a standard curve was plotted from which a correction factor was determined. A correction factor for nitrocellulose was established by mixing amounts of biomass (20, 50, 100, 200 and 300 mg) with 5 ml of the suspension containing 150 mg of nitrocellulose in 35 ml of acetone. Nitrocellulose was precipitated by the addition of water, dried and weighed. The results were used to determine the amount of biomass coprecipitated with nitrocellulose.

Analytical methods:

Chitin was estimated by the procedure of Ride, J. P. and R. B. Drysdale, in "A rapid method for the chemical estimation of filamentous fungi in plant tissue"; Physiol. Plant Pathol. 2:7–15 (1972), and expressed as N-acetylglucosamine. Total sugars were estimated by the phenol-sulfuric acid method by Dubois, M. et al, "Colorimetric method for determination of sugars and related Substances", Anal. Chem. 281: 350–356 (1956), with glucose as the standard. Reducing sugars were estimated by the method of Somogyi, M., "Notes on sugar determination", J. Biol. Chem. 195:19–23 (1952), with glucose as the standard. Glucose was estimated as described in Sigma glucose estimation kit. Soluble protein was estimated by the method of Bradford, M. M., "A refined and sensitive method for the quantitation of microgram quantities protein utilizing the principle of protein-dye binding" Anal. Biochem. 72:248–254 (1976).

Nitrate and nitrite ions were measured by the procedure of Nicholas D., and A. Nason, "Determination of nitrate and nitrite In: Methods in Enzymology", Colowick, S. P. and N. O. Kaplan, eds. Academic Press. NY. III: 981–984 (1957). Aqueous ammonia analyses were performed by Galbraith Laboratories, Inc. Knoxville, Tenn.

RESULTS

Growth of *S. rolfsii* ATCC 24459 and *F. solani* IFO 31093 on nitrocellulose in liquid medium:

The efficacy of *S. rolfsii* ATCC 24459 and *F. solani* IFO 31093 to grow and attack nitrocellulose in liquid medium was evaluated. Nitrocellulose was tested in an amount of 0.3% by weight of the entire medium as the sole source of nitrogen. The results given in Table 1 indicate that aqueous hydrolysis of nitrocellulose at pH 6.0 resulted in the formation of 11.8 micrograms/microliter and 6.5 micrograms/microliter of nitrate and nitrite ions, respectively. Results further demonstrated a more than 45% utilization of nitrite ions by *S. rolfsii* ATCC 24459 and 37% by *F. solani* IFO 31093 in liquid medium. The combined culture, on the other hand, utilized about 70% of the nitrite ions. The soluble nitrate was less effectively utilized by either fungal cultures alone or in combination. A drastic change in pH was also observed in flasks with growing cultures, however, cellulose degrading enzymes could not be detected. Makon NF-5, a non-ionic surfactant, when included into the basal salts medium containing nitrocellulose and starch, enhanced the growth of *S. rolfsii* ATCC 24459. Visual increase in biomass, drastic change in pH, detection of soluble protein, depletion of total sugars, the presence and utilization of nitrate and nitrite ions were indicative measures of growth of *S. rolfsii* ATCC 24459 and *F. solani* IFO 31093 on nitrocellulose. Detection of endo-beta 1,4 -glucanase (Cx) in Makon NF-5 containing culture medium but not in the control (lacking Makon NF-5) indicated that this surfactant facilitates cellulase enzyme transport into the medium.

Time course of nitrocellulose degradation by *S. rolfsii* ATCC 24459 and *F. solani* IFO 31093 in liquid medium

*S. rolfsii* ATCC 24459 secretes cellulose degrading enzymes while *F. solani* IFO 31093 is a denitrifying fungus. Thus attempts were made to determine if combined cultures had the potential to degrade nitrocellulose more efficiently. Both of the fungal cultures were inoculated into the same basal salts medium containing nitrocellulose (0.3%) in the presence or absence of Makon NF-5 and harvested at the different time intervals.

Results of time course of nitrocellulose degradation by *S. rolfsii* ATCC 24459 and *F. solani* IFO 31093 in the presence or absence of Makon NF-5, in liquid medium are given in Tables 2, 3 and 4. An increasing trend of fungal biomass was apparent until day 7 and then declined possibly due to an acidic pH. The formation of clump (mycelia covered with nitrocellulose) was visible where Makon NF-5 was included into the medium. Acetone extraction procedure used for nitrocellulose estimation resulted in the solubilization of fungal biomass. Results indicated a 25% biomass (proteins, lipids, carbohydrates etc.) extraction along with nitrocellulose. Thus, a correction factor had been applied to the reported nitrocellulose results. More than 30% of the nitrocellulose was utilized by growing fungi in a 3 day time period. On a dry weight basis, more than a 4 fold increase in mycelial weight was detected in 3 days irrespective of the presence or absence of Makon NF-5. Fungal biomass (chitin) was determined as N-acetylglucosamine and results given in Table 2 indicate a 25 fold increase in N-acetylglucosamine on day 7 and then a decline. Increase in N-acetylglucosamine was 24 fold on day 3 when Makon NF-5 was included into the medium. Lysis of the biomass was more apparent when Makon NF-5 was included into the basal salts medium. Makon NF-5 assisted enzyme transport into the medium, however it did not enhance nitrocellulose biodegradation.

Significant levels of intracellular denitrifying enzymes such as nitrate and nitrite reductases were also detected in the growing fungal cultures. The activities of both the enzymes increased up to 7 days of cultivation and then nitrate reductase leveled off, whereas nitrite reductase increased marginally. No significant differences in the levels of these enzymes were detected when Makon NF-5 was included into the medium.

TABLE 1

| | | | | | | | | |
|---|---|---|---|---|---|---|---|---|
| Culture | Final pH | Soluble Protein ($\mu$g/ml) | Total Sugars (mg/ml) | Glucose (mg/ml) | beta 1,4-glucanase (U/ml) | Nitrate ($\mu$g/ml) | Nitrite ($\mu$g/ml) | Aq. NH3 (mg/ml) |
| NC Control | 6.0 | 0 | 4.0 | 0.50 | 0 | 11.8 | 6.5 | 1.3 |
| *S. rolfsii* | 4.0 | 0 | 3.1 | 0.04 | 0 | 8.1 | 3.5 | ND |

Growth of Combined Cultures of *S. rolfsii* ATCC 24495 and *F. solani* IFO 31093 on Nitrocellulose in Liquid Medium TABLE 1-continued Growth of Combined Cultures of *S. rolfsii* ATCC 24495 and *F. solani* IFO 31093 on Nitrocellulose in Liquid Medium

| Culture | Final pH | Soluble Protein (μg/ml) | Total Sugars (mg/ml) | Glucose (mg/ml) | beta 1,4-glucanase (U/ml) | Nitrate (μg/ml) | Nitrite (μg/ml) | Aq. NH3 (mg/ml) |
|---|---|---|---|---|---|---|---|---|
| *F. solani* | 6.0 | 0 | 0.3 | 0.08 | 0 | 8.0 | 4.1 | ND |
| *S. rolfsii* + *F. solani* | 3.0 | 0 | 2.3 | 0.01 | 0 | 8.1 | 3.5 | ND |
| *S. rolfsii* + *F. solani** | 2.0 | 0.5 | 0.9 | 0.05 | 0 | 10.4 | 2.0 | 2.1 |
| *S. rolfsii* + *F. solani*** | 2.0 | 1.7 | 0.9 | 0.07 | <0.1 | 14.1 | 1.1 | 3.0 |

*Starch was provided as an additional carbon source
**Makon NF-5 was included into the basal salts medium
ND—Not determined

TABLE 2

Time Course of Fungal Biomass, Nitrate and Nitrite Reductases Production During the Growth of the Combined Cultures (*S. rolfsii* ATCC 24459 and *F. solani* IFO 31093) on Nitrocellulose in Liquid Medium

| Cultivation Time (Days) | Makon NF-5 | Biomass Dry Weight (mg) | N-acetylglucosamine (mg) | N-acetylglucosamine (% of total biomass mg dry weight) | Nitrate reductase (U/ml) | Nitrite reductase (U/ml) |
|---|---|---|---|---|---|---|
| 0 | — | 5.6 | 0.1 | 1.8 | 1.3 | 0.3 |
| 3 | — | 25.5 | 2.0 | 7.8 | 2.6 | 0.9 |
| 3 | + | 23.7 | 2.4 | 10.1 | 2.5 | 0.6 |
| 7 | — | 21.6 | 2.5 | 11.6 | 8.4 | 1.6 |
| 7 | + | 18.0 | 1.7 | 9.4 | 8.1 | 1.4 |
| 14 | — | 20.9 | 0.8 | 3.8 | ND | ND |
| 14 | + | 13.7 | 1.6 | 11.7 | ND | ND |
| 28 | — | 18.0 | 0.6 | 3.3 | 8.4 | 1.7 |
| 28 | + | 12.1 | 0.6 | 4.9 | 8.1 | 1.6 |

Chitin present in the biomass was hydrolysed and determined as N-acetyl-glucosamine
ND—Not determined
Makon NF-5 alone did not support the growth of fungi

TABLE 3

Time Course of Nitrocellulose Utilization by Combined Cultures of *S. rolfsii* ATCC 24459 and *F. solani* IFO 31093 in Liquid Medium Containing Makon NF-5

| Cultivation Time (Days) | Residual Nitrocellulose (mg) Uncorrected | Residual Nitrocellulose (mg) Corrected | Biomass weight (mg) Uncorrected | Biomass weight (mg) Corrected |
|---|---|---|---|---|
| 0 | 150.0 | 150.0 | 6.9 | 6.9 |
| 3 | 118.8 | 106.9 | 20.4 | 25.5 |
| 14 | 106.8 | 96.1 | 15.8 | 19.7 |
| 28 | 108.5 | 97.6 | 9.0 | 11.2 |

Abiotic control on 28 day incubation under identical conditions resulted in 2.5% nitrocellulose loss.

TABLE 4

Time Course of Nitrocellulose Utilization by Combined Cultures of *S. rolfsii* ATCC 24459 and *F. solani* IFO 31093 in Liquid Medium Lacking Makon NF-5

| Cultivation Time (Days) | Residual Nitrocellulose (mg) Uncorrected | Residual Nitrocellulose (mg) Corrected | Biomass dryweight (mg) Uncorrected | Biomass dryweight (mg) Corrected |
|---|---|---|---|---|
| 0 | 150.0 | 150.0 | 6.9 | 6.9 |
| 3 | 115.2 | 103.7 | 16.9 | 21.1 |
| 7 | 118.8 | 106.9 | 16.7 | 23.0 |
| 14 | 116.5 | 104.8 | 15.7 | 19.6 |
| 28 | 108.7 | 97.8 | 10.6 | 13.6 |

Abiotic control on 28 day incubation under identical conditions resulted in 2.5% nitrocellulose loss.

In the past, lack of suitable analytical methods has hampered research on nitrocellulose biodegradation. Prior studies have utilized indirect methods for nitrocellulose estimation. The United States Army Toxic and Hazardous Material Agency's method for nitrocellulose estimation requires digestion of nitrocellulose with alkali followed by nitrate and nitrite estimations by high performance liquid chromatography. This is "USA-THAMA method LY 02, Analysis of nitrocellulose in water". United States Army Toxic and Hazardous Material Agency, Aberdeen Proving Ground, Maryland, USA." Duran, M. et al "Anaerobic biotransformation of nitrocellulose" In: Proceedings on nitrocellulose—fines, separation and treatment, U.S. Army—Purdue University, West Lafayette, Ind. pp. 92–108 (1993); and Hsieh H. N., and F. J. Tai, "Anaerobic digestion and acid hydrolysis of nitrocellulose" Proceedings on nitrocellulose—fines, separation and treatment, U.S. Army—Purdue University, West Lafayette, Ind. pp. 110–121 (1993) measured the quantity of gas produced from nitrocellulose degradation. Based on the detection of reducing sugars during culture growth, IL'Inskaya, A. N. and I. B. Leshehinskaya, "Growth of microorganisms on cellulose nitroesters", Biotekhnologiya. 4:495–500 (1988) concluded that nitrocellulose was degraded under their experimental conditions. Griest W. H., "A proposal for analysis of nitrocellulose in soil or compost" Proceedings of nitrocellulose—fines, separation and treatment, U.S. Army—Purdue University, West Lafayette, Ind. pp. 150–153 (1993), proposed a method for nitrocellulose estimation, although less sensitive, based on the size exclusion chromatography. One of the serious drawback in his methodology was the unavailability of nitrocellulose standards having well defined molecular weights. Gallo, B., et al "Microbial degradation of nitro-cellulose", in: Proceedings on nitrocellulose-fines, separation and treatment, U.S. Army—Purdue University, West Lafayette, Ind. pp. 78–91

(1993), employed another method based on dry weight that involved the separation of nitrocellulose from the fungal biomass by dissolving the former in acetone. The acetone extract was allowed to evaporate and the residual weight was determined. In the present case an acetone extraction procedure was also used. In this case, 25% of the solids from the biomass were extracted along with the nitrocellulose. Therefore, a correction factor was applied to the biomass and nitrocellulose determinations. Brodman, B. W. et al, "Chemical interactions of amino acids and peptides with nitrocellulose and di-n-butyl phthalate", J. Macromol. Sci. Chem. A14:1139–1143 (1980), by using X-Ray photon spectroscopy have demonstrated that nitrocellulose interacts with peptides and amino acids. In this example, 10% of fungal biomass is co-precipitated with nitrocellulose, thus adding to the nitrocellulose weight. Again appropriate corrections were applied to the recovered nitrocellulose weight.

Based on the results obtained in the present invention, it is hypothesized that soluble nitrate and nitrite made available from nitrocellulose and starch, which is provided as a co-substrate, allows *S. rolfsii* ATCC 24459 and *F. solani* IFO 31093 to grow initially. Later, *S. rolfsii* ATCC 24459 starts attacking the cellulosic part of nitrocellulose while the nitro group is denitrated by *F. solani* IFO 31093 to nitrite and $NH_3$. Thirty five percent nitrocellulose was degraded by the combined fungal cultures. During the growth of *S. rolfsii* ATCC 24459 and *F. solani* IFO 31093 on nitrocellulose, a drop in pH (6.0 to 2.0) was measured and it is likely at such a acidic pH, the cellulose degrading enzymes are inactivated.

Detection of soluble protein, cellulolytic and denitrifying enzymes, the presence and depletion of nitrite and total sugars, drastic change in pH (6.0 to 2.0), increase in chitin content and decrease in nitrocellulose weight were indicative of the growth of these two fungi on nitrocellulose. Makon NF-5, a non-ionic surfactant appears to help cellulolytic enzymes to leach out into the medium from the fungal cell wall.

EXAMPLE 2

Several mycelial fungi, including white rotters are screened alone or in combination for nitrocellulose degradation in liquid medium. Soluble starch or beta 1,4-xylan is tested as co-substrates for nitrocellulose degradation. Fungal mycelial mats, from one week old agar culture, are cut into 1.5 cm × 1.5 cm pieces and used as inoculum source for screening experiments. It has been found that *Fusarium solani* IFO 31093, a denitrifying fungus, grows well on nitrocellulose and this example uses nitrocellulose as a sole source of carbon and nitrogen. Starch is used as a co-substrate since it improves the growth of *F. solani* IFO 31093 on nitrocellulose. It has been found that a combination of *F. solani* IFO 31093 with *Sclerotium rolfsii* ATCC 24459, a cellulolytic fungus, results in a significant degradation of nitrocellulose in liquid medium. Pre-grown and washed mycelium of each fungus is homogenized and used as a source of inoculum for the combined culture experiment.

Visual increase of the biomass, drastic change in pH (pH 6.0 to pH 2.0), detection of soluble protein, depletion of nitrite and total sugars are indicative measures of growth of these two fungi on nitrocellulose. Several fold increase in N-acetylglucosamine content (expressed as mg N-acetylglucosamine/mg of biomass dry weight) over a period of time indicates the increase in fungal biomass. An increasing trend of fungal biomass is apparent until the seventh day and then declined possibly due to lysis at acidic pH. This experiment was conducted under aerobic conditions. In the process more than 30% of the NC was degraded in a period of three days.

EXAMPLE 3

Example 2 is repeated except the fungi are also cultivated in the presence of, Makon NF-5, a non-ionic surfactant and results in the formation of clumps of nitrocellulose. Cellulose degrading (beta 1,4-exoglucanase, beta 1,4-endoglucanase and beta-glucosidase) enzymes are detected in the surfactant containing culture medium. Makon NF-5 appears to help the cellulase enzyme complex leach out into the medium from the fungal cell wall and concurrently attacking nitrocellulose. Significant levels of intracellular denitrifying enzymes such as nitrate and nitrite reductases are also detected in the growing cultures.

Analytical determinations performed on controls as well as fungal grown nitrocellulose reveal more than 30% utilization of nitrocellulose by the combined cultures of *S. rolfsii* ATCC 24459 and *F. solani* IFO 31093 in a three day growth period. These degradative rates for nitrocellulose by combined fungal cultures are achieved under aerobic conditions. Further, this result can be likewise expected upon the substitution of other nitrate esters such as nitroglycerin.

Efforts of in-vitro degradation of nitrocellulose by commercially available cellulase alone or in combinations with homogenate of *F. solani* IFO 31093 were unsuccessful. Crude extracellular, intracellular or a combination of both fractions of *S. rolfsii* ATCC 24459 and *F. solani* IFO 31093 also did not attack nitrocellulose.

What is claimed is:

1. A method for degrading nitrate esters which comprises
   a.) forming a suspension of a nitrate ester;
   b.) providing a combination of at least one cellulolytic fungus and at least one denitrifying fungus on a culture growing medium;
   c.) contacting the combination (b) with the suspension of nitrate ester and maintaining the contact for a sufficient time and under conditions sufficient to support lysis and denitrification of the nitrate ester.

2. The method of claim 1 wherein the nitrate ester is nitrocellulose.

3. The method of claim 1 wherein the nitrocellulose is sterilized.

4. The method of claim 3 wherein the nitrocellulose is sterilized by ultraviolet radiation.

5. The method of claim 2 wherein the nitrocellulose contains up to about 14.15% by weight of nitrogen.

6. The method of claim 2 wherein the nitrocellulose contains from about 13.1% to about 13.2% by weight of nitrogen.

7. The method of claim 2 wherein the nitrocellulose suspension further comprises a stabilizer.

8. The method of claim 7 wherein the stabilizer is diphenylamine.

9. The method of claim 1 wherein the nitrate ester is nitroglycerine.

10. The method of claim 1 wherein the suspension is an aqueous suspension.

11. The method of claim 1 wherein the suspension further comprises a surfactant.

12. The method of claim 1 wherein the suspension further comprises a non-ionic surfactant.

13. The method of claim 1 wherein the cellulolytic fungus comprises *Sclerotium rolfsii* ATCC 24459.

14. The method of claim 1 wherein the denitrifying fungus comprises *Fusarium solani* IFO 31093.

15. The method of claim 1 wherein the growing medium comprises at least one natural polysaccharide.

16. The method of claim 1 wherein the growing medium comprises starch.

17. The method of claim 1 wherein step (c) is conducted in the presence of air.

18. The method of claim 1 wherein step (c) is conducted for from about 3 to about 10 days.

19. A method for degrading nitrocellulose which comprises
 a.) forming an aqueous suspension of a nitrocellulose;
 b.) providing a combination of *Sclerotium rolfsii* ATCC 24459 and *Fusarium solani* IFO 31093 on a culture growing medium; and
 c.) contacting the combination (b) with the nitrocellulose suspension and maintaining the contact for a sufficient time and under conditions sufficient to support lysis and denitrification of the nitrocellulose.

20. The method of claim 19 wherein the aqueous suspension further comprises a non-ionic surfactant.

21. The method of claim 19 wherein step (c) is conducted in the presence of air for from about 3 to about 10 days.

* * * * *